United States Patent
Shu et al.

(10) Patent No.: US 11,448,654 B2
(45) Date of Patent: Sep. 20, 2022

(54) PROTEIN-PROTEIN INTERACTION ASSESSED BY DETECTING LOCALIZED COILED COIL SUBUNITS

(71) Applicant: The Regents of the University of California, Oakland, CA (US)

(72) Inventors: Xiaokun Shu, San Francisco, CA (US); Qiang Zhang, Daly City, CA (US); Chan-I Chung, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 369 days.

(21) Appl. No.: 16/838,023

(22) PCT Filed: Oct. 2, 2018

(86) PCT No.: PCT/US2018/053972
§ 371 (c)(1),
(2) Date: Apr. 1, 2020

(87) PCT Pub. No.: WO2019/070711
PCT Pub. Date: Apr. 11, 2019

(65) Prior Publication Data
US 2021/0215708 A1 Jul. 15, 2021

Related U.S. Application Data

(60) Provisional application No. 62/567,382, filed on Oct. 3, 2017, provisional application No. 62/671,403, filed on May 14, 2018.

(51) Int. Cl.
| | |
|---|---|
| *G01N 33/68* | (2006.01) |
| *C12N 9/12* | (2006.01) |
| *C07K 14/47* | (2006.01) |
| *C12N 9/06* | (2006.01) |
| *G01N 33/542* | (2006.01) |
| *G01N 33/58* | (2006.01) |

(52) U.S. Cl.
CPC ..... *G01N 33/6845* (2013.01); *C07K 14/4705* (2013.01); *C07K 14/4746* (2013.01); *C12N 9/0028* (2013.01); *C12N 9/12* (2013.01); *G01N 33/542* (2013.01); *G01N 33/582* (2013.01)

(58) Field of Classification Search
CPC .............................. G01N 33/6846; C12N 9/12
USPC ............................................................ 435/7
See application file for complete search history.

(56) References Cited

U.S. PATENT DOCUMENTS

| 9,562,074 B2 | 2/2017 | Woolfson et al. |
| 2006/0257887 A1 | 11/2006 | Waldo |

FOREIGN PATENT DOCUMENTS

| WO | 9902707 A2 | 1/1999 |

OTHER PUBLICATIONS

Mitrea, Diana M. et al., 'Phase separation in biology; functional organization of a higher order', Cell Communication and Signaling, 2016, vol. 14, No. 1, pp. 1-20. See the entire document.
Mier, Pablo et al., 'Protein-protein interactions can be predicted using coiled coil co-evolution patterns', Journal of Theoretical Biology, 2017(published online: Nov. 7, 2016), vol. 412, pp. 198-203. See the entire document.

*Primary Examiner* — Sheridan Swope

(57) ABSTRACT

The invention is a novel reporter system for measuring protein-protein interactions. The system uses a pair of functionalized coiled coil subunits that spontaneously form two separate homo-oligomers when expressed in cells. The coiled coil subunits are functionalized with fluorescent proteins and complementary interacting proteins. Upon an activation stimulus which promotes the protein-protein interaction, the interacting proteins drive the formation of multivalent aggregates of the homo-oligomers in phase-shifted droplets. The highly concentrated fluorescent proteins in these structures provide high brightness over background fluorescence and a readily observed, quantitative and dynamic indicator of the protein-protein interaction. The reporters and assay methods are amenable to cells and whole organisms.

20 Claims, 7 Drawing Sheets
Specification includes a Sequence Listing.

SEQUENCE LISTING

```
<160> NUMBER OF SEQ ID NOS: 19

<210> SEQ ID NO 1
<211> LENGTH: 33
<212> TYPE: PRT
<213> ORGANISM: Artificial Sequence
<220> FEATURE:
<223> OTHER INFORMATION: Description of Artificial Sequence: Synthetic
      HOTag 1

<400> SEQUENCE: 1

Thr Gln Glu Asp Leu Leu Lys Lys Ile Met Lys Leu Leu Lys Lys Gln
1               5                   10                  15

Ile Lys Leu Leu Lys Lys Gln Ile Lys Met Leu Lys Arg Leu Glu Lys
            20                  25                  30

Gln

<210> SEQ ID NO 2
<211> LENGTH: 30
<212> TYPE: PRT
<213> ORGANISM: Artificial Sequence
<220> FEATURE:
<223> OTHER INFORMATION: Description of Artificial Sequence: Synthetic
      HOTag 2

<400> SEQUENCE: 2

Gly Glu Ile Ala Gln Ala Leu Lys Glu Ile Ala Lys Ala Leu Lys Glu
1               5                   10                  15

Ile Ala Trp Ala Leu Lys Glu Ile Ala Gln Ala Leu Lys Gly
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Description of Artificial Sequence: Synthetic
      HOTag 3

<400> SEQUENCE: 3

Gly Glu Ile Ala Lys Ser Leu Lys Glu Ile Ala Lys Ser Leu Lys Glu
1               5                   10                  15

Ile Ala Trp Ser Leu Lys Glu Ile Ala Lys Ser Leu Lys Gly
            20                  25                  30

<210> SEQ ID NO 4
<211> LENGTH: 30
<212> TYPE: PRT
<213> ORGANISM: Artificial Sequence
<220> FEATURE:
```

<223> OTHER INFORMATION: Description of Artificial Sequence: Synthetic
      HOTag 4

<400> SEQUENCE: 4

Gly Lys Ile Glu Gln Ile Leu Gln Lys Ile Glu Lys Ile Leu Gln Lys
1               5                   10                  15

Ile Glu Trp Ile Leu Gln Lys Ile Glu Gln Ile Leu Gln Gly
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic
      HOTag 5

<400> SEQUENCE: 5

Ala Glu Ala Glu Ser Ala Leu Glu Tyr Ala Gln Gln Ala Leu Glu Lys
1               5                   10                  15

Ala Gln Leu Ala Leu Gln Ala Ala Arg Gln Ala Leu Lys Ala
            20                  25                  30

<210> SEQ ID NO 6
<211> LENGTH: 33
<212> TYPE: PRT
<213> ORGANISM: Artificial Sequence
<220> FEATURE:
<223> OTHER INFORMATION: Description of Artificial Sequence: Synthetic
      HOTag 6

<400> SEQUENCE: 6

Thr Leu Arg Glu Ile Glu Glu Leu Leu Arg Lys Ile Ile Glu Asp Ser
1               5                   10                  15

Val Arg Ser Val Ala Glu Leu Glu Asp Ile Glu Lys Trp Leu Lys Lys
            20                  25                  30

Ile

<210> SEQ ID NO 7
<211> LENGTH: 32
<212> TYPE: PRT
<213> ORGANISM: Artificial Sequence
<220> FEATURE:
<223> OTHER INFORMATION: Description of Artificial Sequence: Synthetic
      HOTag 7

<400> SEQUENCE: 7

Gly Glu Leu Ala Ala Ile Lys Gln Glu Leu Ala Ala Ile Lys Lys Glu
1               5                   10                  15

Leu Ala Ala Ile Lys Trp Glu Leu Ala Ala Ile Lys Gln Gly Ala Gly
            20                  25                  30

<210> SEQ ID NO 8
<211> LENGTH: 34
<212> TYPE: PRT
<213> ORGANISM: Artificial Sequence
<220> FEATURE:
<223> OTHER INFORMATION: Description of Artificial Sequence: Synthetic
      HOTag 8

<400> SEQUENCE: 8

Met Lys Val Lys Gln Leu Glu Asp Val Val Glu Glu Leu Leu Ser Val
1               5                   10                  15

Asn Tyr His Leu Glu Asn Val Val Ala Arg Leu Lys Lys Leu Val Gly

Glu Arg

<210> SEQ ID NO 9
<211> LENGTH: 33
<212> TYPE: PRT
<213> ORGANISM: Artificial Sequence
<220> FEATURE:
<223> OTHER INFORMATION: Description of Artificial Sequence: Synthetic
      HOTag 9

<400> SEQUENCE: 9

Thr Gln Glu Tyr Leu Leu Lys Glu Ile Met Lys Leu Leu Lys Glu Gln
1               5                   10                  15

Ile Lys Leu Leu Lys Glu Gln Ile Lys Met Leu Lys Glu Leu Glu Lys
            20                  25                  30

Gln

<210> SEQ ID NO 10
<211> LENGTH: 52
<212> TYPE: PRT
<213> ORGANISM: Artificial Sequence
<220> FEATURE:
<223> OTHER INFORMATION: Description of Artificial Sequence: Synthetic
      HOTag 10

<400> SEQUENCE: 10

Gly Ser Ile Ile Asn Glu Thr Ala Asp Asp Ile Val Tyr Arg Leu Thr
1               5                   10                  15

Val Ile Ile Asp Asp Arg Tyr Glu Ser Leu Lys Asn Leu Ile Thr Leu
            20                  25                  30

Arg Ala Asp Arg Leu Glu Met Ile Ile Asn Asp Asn Val Ser Thr Ile
        35                  40                  45

Leu Ala Ser Ile
    50

<210> SEQ ID NO 11
<211> LENGTH: 30
<212> TYPE: PRT
<213> ORGANISM: Artificial Sequence
<220> FEATURE:
<223> OTHER INFORMATION: Description of Artificial Sequence: Synthetic
      HOTag 11

<400> SEQUENCE: 11

Gly Glu Ile Ala Ala Ile Lys Gln Glu Ile Ala Ala Ile Lys Lys Glu
1               5                   10                  15

Ile Ala Ala Ile Lys Trp Glu Ile Ala Ala Ile Lys Gln Gly
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: Description of Artificial Sequence: Synthetic
      HOTag 12

<400> SEQUENCE: 12

Gly Glu Ile Ala Ala Leu Lys Gln Glu Ile Ala Ala Leu Lys Lys Glu
1               5                   10                  15

Asn Ala Ala Leu Lys Trp Glu Ile Ala Ala Leu Lys Gln Gly
            20                  25                  30

<210> SEQ ID NO 13
<211> LENGTH: 29
<212> TYPE: PRT
<213> ORGANISM: Artificial Sequence
<220> FEATURE:
<223> OTHER INFORMATION: Description of Artificial Sequence: Synthetic
      HOTag 13

<400> SEQUENCE: 13

Glu Val Glu Ala Leu Glu Lys Lys Val Ala Ala Leu Glu Ser Lys Val
1               5                   10                  15

Gln Ala Leu Glu Lys Lys Val Glu Ala Leu Glu His Gly
            20                  25

<210> SEQ ID NO 14
<211> LENGTH: 44
<212> TYPE: PRT
<213> ORGANISM: Artificial Sequence
<220> FEATURE:
<223> OTHER INFORMATION: Description of Artificial Sequence: Synthetic
      HOTag 14

<400> SEQUENCE: 14

Lys Gln Leu Glu Lys Glu Leu Lys Gln Leu Glu Lys Glu Leu Gln Ala
1               5                   10                  15

Ile Glu Lys Gln Leu Ala Gln Leu Gln Trp Lys Ala Gln Ala Arg Lys
            20                  25                  30

Lys Lys Leu Ala Gln Leu Lys Lys Lys Leu Gln Ala
        35                  40

<210> SEQ ID NO 15
<211> LENGTH: 29
<212> TYPE: PRT
<213> ORGANISM: Artificial Sequence
<220> FEATURE:
<223> OTHER INFORMATION: Description of Artificial Sequence: Synthetic
      HOTag 15

<400> SEQUENCE: 15

Glu Trp Glu Ala Leu Glu Lys Lys Leu Ala Ala Leu Glu Ser Lys Leu
1               5                   10                  15

Gln Ala Leu Glu Lys Lys Leu Glu Ala Leu Glu His Gly
            20                  25

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      Linker element

<400> SEQUENCE: 16

Gly Gly Gly Gly Ser
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus peptide sequence phosphorylated by PKA

<400> SEQUENCE: 17

```
Leu Arg Arg Ala Thr Leu Val Asp
1               5

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      E3 ligase recognition domain

<400> SEQUENCE: 18

Asp Arg His Asp Ser Gly Leu Asp Ser Met
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      E3 ligase recognition domain

<400> SEQUENCE: 19

Ala Leu Ala Pro Tyr Ile Pro
1               5
```

PROTEIN-PROTEIN INTERACTION ASSESSED BY DETECTING LOCALIZED COILED COIL SUBUNITS

CROSS REFERENCE TO RELATED APPLICATIONS

This application claims the benefit of priority of PCT International Patent Application PCT/US2018/053972, entitled "Phase Separation Based Reporters of Protein-Protein Interactions," filed Oct. 2, 2018, which claims priority to both U.S. Provisional Patent Application No. 62/567,382 Filed Oct. 3, 2017, entitled "Phase Separation Based Reporters of Protein-Protein Interactions," and U.S. Provisional Patent Application No. 62/671,403, entitled "Phase Separation Based Reporters of PROTAC-induced PPI's," filed May 14, 2018, all of which are incorporated by reference in their entirety.

STATEMENT REGARDING FEDERALLY SPONSORED RESEARCH OR DEVELOPMENT

This invention was made with government support under grant No. GM105446 awarded by the National institutes of Health. The government has certain rights in the invention.

REFERENCE TO SEQUENCE LISTING, A TABLE, OR A COMPUTER PROGRAM LISTING COMPACT DISK APPENDIX

The instant application contains a Sequence Listing which has been filed electronically in ASCII format and is hereby incorporated by reference in its entirety. Said ASCII copy, created on Sep. 27, 2018, is named UCSF050PCT_SL.txt and is 7,765 bytes in size.

BACKGROUND OF THE INVENTION

The monitoring of protein-protein interactions in living cells is a vital endeavor in biological and medical research. Various research tools have been developed for the study of such interaction in vivo, such as Forster resonance energy transfer (FRET) reporters and bimolecular fluorescence complementation assays. However, the tools developed to date suffer from the complications of imaging dispersed fluorescent proteins in living cells and animals. Signal measurement and interpretation is challenging with current assays due to low fluorescence changes, complex signal patterns, tissue autofluorescence, light scattering, and rapid cell movement and shape changes.

Meanwhile, in natural systems, phase-separated droplets formed by multivalent proteins create distinct structures within the cell, with unique microenvironments that can facilitate certain enzymatic activities. The prevalence and importance of these phase-separated bodies in biology has only recently been appreciated. In a recapitulation of these natural systems, Li et al., (2012), Phase transitions in the assembly of multivalent signaling proteins. Nature 483, 336-340, constructed artificial multivalent reporters of protein-protein interactions, comprising reporter proteins functionalized with multiple copies of two interacting proteins. When the protein-protein interactions were induced, the reporter proteins aggregated, creating localized phase separated bodies in living cells that were readily observed.

Li's work demonstrated the potential of synthetic multivalent proteins as indicators of protein-protein interactions. However, Li's reporter proteins comprised large, bulky proteins having several repeating protein domains. Applying the reporter system of Li is problematic because the efficient expression of such large proteins is difficult, and the size of the reporter constructs can hinder the protein-protein interactions to be studied. Furthermore, the repeating domains used in this prior method are problematic for making transgenic animals due to the high potential for DNA recombination.

Accordingly, there remains a need in the art for superior assays for probing protein-protein interactions. There is a need for a more efficient, customizable platform for reporting protein-protein interactions. There is a need for more robust fluorescent reporters for detecting and imaging protein-protein interactions. There is a need for detecting and imaging these protein-protein interactions in various situations, including in vivo imaging within living animals. There is a need for a fluorescent protein-protein interaction reporter that has a large signal-to-noise ratio and fast kinetics. There is a need for novel synthetic multivalent proteins which can act as indicators of selected protein-protein interactions by the formation of phase-separated intracellular droplets, wherein such reporters are efficiently expressed and wherein such systems are highly customizable and effective.

SUMMARY OF THE INVENTION

The various inventions disclosed herein fulfill the aforementioned needs in the art. The present invention encompasses novel reporters of protein-protein interactions. The overall operation and objective of the invention encompasses the use of two functionalized orthogonal monomers, each one comprising one partner of a protein-protein interaction. The monomers can be readily expressed together in cells wherein homo-oligomers of the two monomer types will form. Upon the occurrence of the protein-protein interaction, the homo-oligomers will cross-link by the binding of the interacting protein partners. The result is a localized network of highly condensed oligomers which results in phase shifting and the segregation of bright signal in distinct punctae.

In a primary implementation, the invention employs compact, coiled coil based monomers. In the practice of the invention, two different types of coiled coil oligomeric monomers are made, each type functionalized with complementary partners of a targeted protein-protein interaction, and being further functionalized with at least one fluorescent protein. In living cells, expression of the reporter proteins results in the spontaneous formation of oligomeric reporter assemblies, each comprising several copies of one of the interacting proteins and at least one of the pair comprising several copies of a fluorescent protein reporter. When the protein-protein interaction is activated, the interacting proteins of each oligomer will be connected to multiple copies of the complementary oligomer by the interactions of the complementary proteins. Multivalent complexes are formed that concentrate the fluorescent labels in phase-separated intracellular droplets. These localized and intense punctae are readily visualized and quantified. The kinetics of the multivalent complex formation are fast and efficient. The reporter proteins may be readily expressed and imaged in cells and living organisms.

The novel inventions of the present disclosure improve upon the prior art by the use of coiled coil subunits as the backbone of the oligomeric reporter elements. As set forth below, the use of coiled coil proteins has numerous advantages, providing the art with an effective and versatile system for monitoring protein-protein interactions.

In one aspect, the scope of the invention encompasses novel reporter constructs comprising coiled coil proteins which may be customized and used to detect a selected protein-protein interaction. In the presence of the reporter system, the selected interaction creates multivalent complexes and readily visualized signals in phase-shifted droplets.

In one aspect, the scope of the invention encompasses novel genetic constructs and engineered cells and organisms which express the reporter constructs of the invention.

In one aspect, the scope of the invention encompasses methods of observing and/or quantifying a target protein-protein interaction and provides methods for elucidating the factors that modulate the target protein-protein interaction or testing modulators of the selected interaction.

In one aspect, the scope of the invention encompasses novel tools for measuring the activity of enzymes, wherein the protein-protein interaction are driven by the activity of the enzyme.

In one embodiment, the invention encompasses novel tools for detecting kinase activity. Kinase-substrate interactions serve as major control points for innumerable biological processes. In certain implementations, the constructs of the invention can be used to monitor kinase interactions with substrates.

In one aspect, the scope of the invention encompasses novel tools for measuring the activity of proteolysis targeting chimera (PROTAC) constructs, which are chimeric molecules designed to specifically degrade target proteins. The reporters of the invention encompass constructs and methods for evaluating and improving PROTACs and like tools.

BRIEF DESCRIPTION OF THE FIGURES

FIG. 1A depicts an exemplary reporter system expressed as a single fusion protein comprising two separate reporter monomers. The first monomer comprises a first, hexamer-forming HOTag3 coiled coil subunit 101 joined to a fluorescent protein 102 and a first interacting protein 103, which in this example is a sequence phosphorylated in the presence of the kinase PKA. The first monomer sequence is joined to the second monomer sequence by a self-cleaving moiety 104. The second monomer comprises a second, tetramer-forming coiled coil HOTag6 subunit 105 and a second interacting protein 106, which in this example is the forkhead associated domain HFA1. HFA1 interacts with the first interacting protein 104 only when the first interacting protein is phosphorylated. The elements are joined by linker sequences 107. The construct of FIG. 1A may be expressed as a single protein, wherein cleavage of the self-cleaving moiety results in the monomers being separated after expression.

FIG. 1C depicts the second oligomeric reporter 113, which is complementary to the first reporter oligomer 112 of FIG. 1B, formed of monomers 111 by the spontaneous oligimerization of the second coiled coil subunit 105, in this example, in this example, the oligomeric reporter being a tetramer comprising four copies of the first subunit 105 and four copies of the second interacting protein 106.

FIG. 1D depicts a plurality of first oligomeric reporters 112 and second oligomeric reporters 113, wherein the phosphorylated first interacting protein 103 and the second interacting protein 106 are interacting, connecting each oligomeric reporter to two or more complementary oligomeric reporters. This aggregation of the reporter proteins results in the formation of a microdroplet structure 114 and an intense localized concentration of the fluorescent reporter molecule 102.

FIGS. 2A, 2B, 2C, and 2D depict the elements of an exemplary PROTAC reporter system of the invention. FIG. 2A depicts a first oligomeric reporter 212 comprising a hexamer of monomers, each monomer comprising a HOTag3 coiled coil subunit 201 functionalized with a fluorescent protein 202 and a first interacting protein 203 comprising an E3 ubiquitin ligase. FIG. 2B depicts a second oligomeric reporter 213 which is a tetramer of monomers, each monomer comprising a HOTag6 coiled coil subunit 205 functionalized with a fluorescent protein 209 and a second interacting protein 210 comprising cereblon. FIG. 2C depicts an ARV-825 PROTAC construct 206, comprising a domain 214 that binds E3 ubiquitin ligase and a domain 215 that binds cereblon. In FIG. 2D, the oligomeric reporters 212 and 213 are co-expressed or utilized with a plurality of PROTAC constructs 206. By the interactions between the PROTAC construct 206 and the first 203 and second 210 interacting proteins, each oligomer becomes joined to two or more complementary oligomers. This results in the formation of a microdroplet structure 214 and an intense localized concentration of the fluorescent proteins 202 and 205.

FIGS. 3A, 3B, 3C, 3D, 3E, and 3F depict a quantification technique for measuring signal. Each of FIGS. 3A, 3B, and 3C depicts a selected field of view 101 of an imaged cell at three time points. In FIGS. 3A, 3B, and 3C, a line 302 is drawn through the field of view at a selected cross section of the cell. FIG. 3A depicts an image obtained prior to an activating stimulus, wherein no punctae have been formed. FIG. 3B depicts an image obtained shortly after an activating treatment is applied to the cell, wherein small punctae are forming within the cell, including two punctae, 303 and 304, that intersect the line. FIG. 3C depicts the field of view after full formation of droplets is achieved, wherein the punctae have grown in size and intensity. By image analysis, signal intensity (e.g. measured in arbitrary units) is measured across the distance of the line (e.g., measured in pixels). FIGS. 3D, 3E, and 3F are histogram plots of signal intensity vs. distance along the line, created for each time point imaged in FIGS. 3A, 3B, and 3C respectively. In FIG. 3D, the only signal across the line is background signal, which is homogenously dispersed. In FIG. 3E, two peaks in signal intensity corresponding to punctae 303 and 304 are observed. In FIG. 3F, the peaks corresponding to punctae 303 and 304 have increased in size due to the increase in droplet size and intensity.

DETAILED DESCRIPTION OF THE INVENTION

Figure 1A:
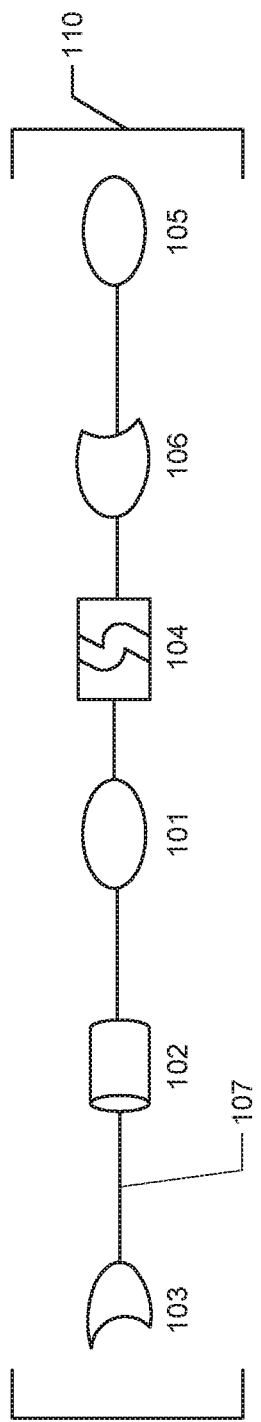
FIG. 1A.

The reporter system of the invention comprises a pair of complementary components. The two complementary components are referred to herein as reporter monomers, which, for reference, will be referred to as a first monomer and a second monomer. Each monomer is a fusion protein made up of multiple elements, including a coiled coil subunit, an interacting protein, and, for at least one monomer of the pair, a fluorescent protein or another reporter moiety. For reference, the coiled coil subunit and the interacting protein of the first monomer will be referred to as the first subunit and the first interacting protein. Likewise, the coiled coil subunit and the interacting protein of the second monomer will be referred to as the second subunit and the second interacting protein.

When expressed in a cell, numerous copies of each monomer will be produced. By energetically favored interactions of the coiled coil subunits, each monomer type will spontaneously oligomerize to form homo-oligomers, the valency of which is determined by the subunit sequences. Homo-oligomers of the first monomer will be referred to as the first oligomeric reporter and homo-oligomers of the second oligomeric reporter will be referred to as the second oligomeric reporter. Each element of the system, and methods of using the reporters, is described next.

Coiled Coil Subunits. As set forth above, each reporter monomer comprises a coiled coil subunit. The novel use of coiled coils as reporter oligomer subunits provides many advantages, including efficient expression and effective formation of phase-shifted droplets. A coiled-coil subunit is an alpha helical polypeptide sequence that, in the presence of identical subunits, will spontaneously form coiled coil oligomers of intertwining alpha helices. Valency of the oligomers is determined by the sequence of the subunit, wherein each subunit type forms an energetically favored oligomeric structure. Thus, as dictated by the subunit's polypeptide sequence, under physiological conditions, for example, when expressed in a cell, coiled coil subunits of the invention will form an oligomer consisting of a dimer, a trimer, a tetramer, a pentamer, a hexamer, a heptamer, or an octomer or higher order oligomer.

The oligomer-forming subunits of the invention comprise coiled coil protein sequences. The coiled coil subunits may comprise any alpha helical polypeptide that will spontaneously form a coiled coil oligomer with other subunits of the same sequence under physiological conditions. Coiled coil structures are formed by the interactions of repeating nonpolar amino acids on the subunits, spaced in an arrangement that facilitates packing with one or more additional subunits of the same sequence. The subunits may align in parallel or antiparallel configurations. The subunits will self-assemble into homo-oligomers by side-chain interactions forming salt bridges and solvent-driven formation of a hydrophobic core.

Any coiled coil subunit capable of forming homo-oligomers of two or more subunits may be used in the practice of the invention. Preferred subunit polypeptide sequences are those that will form oligomers, which are highly water soluble, and which will not spontaneously form phase-shifted droplets, even at high concentrations. Preferred coiled coil structures have 3-8 subunit helices. Preferred subunits are small in size, such that the resulting homo-oligomer formed thereby is relatively compact. Subunits comprising, for example, 15-40 amino acids, for example 20-35 amino acids may be used. Additionally, preferred subunit sequences are those that do not substantially interact with endogenous proteins found in cells.

Exemplary coiled coil subunits include the enumerated subunit sequences provided herein, referred to herein as Homo-Oligomeric Tags ("HOTags"). HOTag sequences include SEQ ID NO: 1-SEQ ID NO: 15. These sequences are previously known protein sequences characterized in protein de nova design studies including: Grigoryan et al., (2011). Computational design of virus-like protein assemblies on carbon nanotube surfaces. Science 332, 1071-1076; Huang et al., (2014). High thermodynamic stability of parametrically designed helical bundles. Science 346, 481-485; and Thomson et al. (2014). Computational design of water-soluble α-helical barrels. Science 346, 485-488.

In one embodiment, the subunit comprises SEQ ID NO: 1, denoted HOTag1, having the sequence: TQEDLLK-KIMKLLKKQIKLLKKQIKMLKRLEKQ and which forms a pentamer.

In one embodiment, the subunit comprises SEQ ID NO: 2, denoted HOTag2, having the sequence: GEIAQALKE-IAKALKEIAWALKEIAQALKG, and which forms a heptamer.

In one embodiment, the subunit comprises SEQ ID NO: 3, denoted HOTag3, having the sequence: GEIAKSLKE-IAKSLKEIAWSLKEIAKSLKG, and which forms a hexamer.

In one embodiment, the subunit comprises SEQ ID NO: 4, denoted HOTag4, having the sequence: GKIEQILQK-IEKILQKIEWILQKIEQILQG, and which forms a pentamer.

In one embodiment, the subunit comprises SEQ ID NO: 5, denoted HOTag5, having the sequence: AEAESA-LEYAQQALEKAQLALQAARQALKA, and which forms a tetramer.

In one embodiment, the subunit comprises SEQ ID NO: 6, denoted HOTag6, having the sequence: TLREIEELLRKIIEDSVRSVAELEDIEKWLKKI, and which forms a tetramer.

In one embodiment, the subunit comprises SEQ ID NO: 7, denoted HOTag7, having the sequence: GELAAIKQE-LAAIKKELAAIKWELAAIKQGAG, and which forms a tetramer.

In one embodiment, the subunit comprises SEQ ID NO: 8, denoted HOTag8, having the sequence: MKVKQLEDVVEELLSVNYHLENVVARLKKLVGER, and which forms a tetramer In one embodiment, the subunit comprises SEQ ID NO: 9, denoted HOTag 9, having the sequence: TQEYLLKE-IMKLLKEQIKLLKEQIKMLKELEKQ, and which forms a pentamer.

In one embodiment, the subunit comprises SEQ ID NO: 10, denoted HOTag10, having the sequence: GSIINETAD-DIVYRLTVIIDDRYESLKNLITLRADRLEMIINDNVS-TILASI, and which forms a tetramer.

In one embodiment, the subunit comprises SEQ ID NO: 11, denoted HOTag 11, having the sequence: GEIAAIKQE-IAAIKKEIAAIKWEIAAIKQ, and which forms a trimer.

In one embodiment, the subunit comprises SEQ ID NO: 12, denoted HOTag12, having the sequence: GEIAALKQE-IAALKKENAALKWEIAALKQG, and which forms a dimer.

In one embodiment, the subunit comprises SEQ ID NO: 13, denoted HOTag 13, having the sequence: EVEALEKK-VAALESKVQALEKKVEALEHG, and which forms a dimer.

In one embodiment, the subunit comprises SEQ ID NO: 14, denoted HOTag14, having the sequence: KQLEKELKQLEKELQAIEKQLAQLQWKAQARKKKL AQLKKKLQA, and which forms a trimer.

In one embodiment, the subunit comprises SEQ ID NO: 15, denoted HOTag, 15 having the sequence: EWEALEKK-LAALESKLQALEKKLEALEHG, and which forms a trimer.

In one embodiment, the reporter system comprises a pair of reporter monomers comprising two coiled coil subunit sequences selected from the group consisting of HOTag 1-HOTag 15. In one embodiment, the selected sequences comprise SEQ ID NO: 3 (HOTag3) and SEQ ID NO: 6 (HOTag 6).

The subunits may comprise the various sequences disclosed above. The scope of the invention further extends to any other polypeptide sequence that will form a coiled coil or coiled coil-like oligomeric structure, as known in the art. The subunits may comprise alpha helical protein domains found in nature or may comprise engineered sequences designed by methods known in the art. The scope of the invention further encompasses variants of the enumerated sequences of SEQ ID NO: 1-15, including substitutions with other amino acids, including non-natural amino acids, additions, deletions, etc, to the extent that coiled coil homo-oligomeric structures are formed by the modified sequences. Variants may comprise sequences having at least 75%, at least 80%, at least 85%, at least 90%, at least 95% or at least 99% sequence identity to a sequence selected from SEQ ID NO: 1 through SEQ ID NO: 15.

While the use of subunits forming homo-oligomers is simple and preferred, in a variation of the invention, hetero-oligomers comprising two or more different subunit sequences that form stable hetero-oligomers may be utilized, wherein the two or more subunits are identically functionalized.

Interacting Proteins. The reporter systems of the invention are directed to the detection of a selected protein-protein interaction. The protein-protein interaction will encompass the interaction of two proteins, referred to herein as the first interacting protein and the second interacting protein, or referred to as the interacting protein partners. A protein-protein interaction, as known in the art, is an energetically favored contact or physical association between elements of the interacting proteins. For example, if the selected protein-protein interaction is an enzyme-substrate interaction, the first interacting protein can be the enzyme and the second interacting protein can be the substrate.

In the reporter systems of the invention, each monomer of the reporter system comprises a coiled coil subunit functionalized with an interacting protein. As used herein, functionalized means fused in a continuous polypeptide sequence with. Fusion constructs optionally comprise an intervening linker sequence between the fused elements. For reference, the first monomer of the system will comprise a first coiled coil subunit functionalized with a first interacting protein. The first interacting protein comprises a polypeptide sequence and has a capacity to interact in a protein-protein interaction with the second interacting protein. Likewise, the second monomer of the system will comprise a second coiled coil subunit functionalized with a second interacting protein comprising, wherein the second interacting protein comprises a polypeptide sequence and has a capacity to interact in a protein-protein interaction with the first interacting protein.

The interacting proteins may comprise any protein sequence, for example, from 10-10,000 amino acids. In some implementations, for observation of a selected protein-protein interaction, the entire native protein sequences of the interacting proteins are utilized. In other implementations, active portions of two interacting proteins are utilized, resulting in a more compact reporter system. For example, the first and second interacting proteins may comprise truncated versions of the proteins of interest or fragments therefore, for example, a domain or subunit of a protein, for example a sequence comprising a binding motif, a catalytic domain, etc.

In one implementation of the invention, one or both of the interacting proteins is an "activable" protein. An activable protein is an interacting protein that does not substantially interact with its complementary partner, unless activated. Upon activation, the activable interacting protein becomes an activated interacting protein that can interact with its partner. Activation may comprise any chemical or biological process, which changes the affinity or activity of the activable protein partner for its complementary protein partner such, that it will interact therewith. Examples of activation include phosphorylation, dephosphorylation, methylation, glycosylation, oxidation, reduction, binding of co-factors, displacement of ligands, conformational changes, etc. Activation may be directly driven by an activating species such as a drug, a cofactor, or biological molecule (e.g. binding protein, nucleic acid, pathogen, etc.). Alternatively, activation may occur as a result of changes in the microenvironment, e.g. changes in pH, oxygenation, redox balance, presence of certain ions, etc. Activation may occur as the result of developmental changes in the cells or organisms wherein the reporter is deployed, for example after the passage of time or developmental milestones. Typically, only a single activable protein is used, but both the interacting protein partners may be activable in other implementations.

In one embodiment, interacting protein(s) comprises an activable species activated by an enzyme. Activation of the activable species by the action of the enzyme directly results in measurable protein-protein interactions between the interacting partners. Thus, the use of enzyme-activable interacting proteins enables the use of the reporter system as a tool to measure the activity of the enzyme. In one embodiment, the enzyme is a kinase and one of the activable interacting proteins is a kinase substrate that is specifically phosphorylated by the kinase. In one embodiment, the enzyme is a phosphatase.

In an alternative embodiment, one of the interacting proteins comprises a binding moiety which will bind a selected target species, wherein the bound species will participate in an interaction with the other interacting protein partner. Exemplary binding moieties include binding domains of ligands, nucleic acid binding domains, and antigen binding domains derived from antibodies. The use of the binding moiety enables the participation of species targeted thereby in an interaction. This may be useful wherein expression of the target species in a fusion protein with the subunit is problematic. For example, if the selected species is not a protein (e.g. is a nucleic acid, pathogen, or other composition), is too large or otherwise poorly expressed, the use of a binding moiety that binds the target species enables its use in an interaction assay. In this implementation of the invention, rather than a protein-protein interaction, a protein-target interaction may be assayed, wherein the target is a non-protein species such as a nucleic acid, lipid, virus, pathogen, small molecule, co-factor, etc.

Reporter Moiety. In the systems of the invention, one or both of the subunits will be functionalized with a reporter moiety. One or more reporter moieties may be present on the functionalized monomer. A preferred reporter moiety is a fluorescent protein. As described below, highly concentrated fluorescent proteins provide easily visualized points or punctae for quantifying the selected protein-protein interaction. In one implementation, only one of the two subunit types is functionalized with a fluorescent reporter. In an alternative embodiment, both are functionalized with a fluorescent reporter. In this configuration, both subunits may be functionalized with the same fluorescent label, or they may comprise different fluorescent proteins to emit multicolored signals. Exemplary fluorescent proteins include, for example, GFP, EGFP, and other GFP variants, mNeon, mOrange, mKO2, tdTomato, mCherry, FusionRed, mApple, or infrared fluorescent proteins such as IFP2.0 or mIFP. It will be understood that the scope of the invention further encompasses reporter moieties other than fluorescent proteins, encompassing any protein that can directly or indirectly generate a measurable signal, including for example, enzymatic reporters such as luciferase or epitopes for the hinging of labeled antibodies.

Figure 1B:
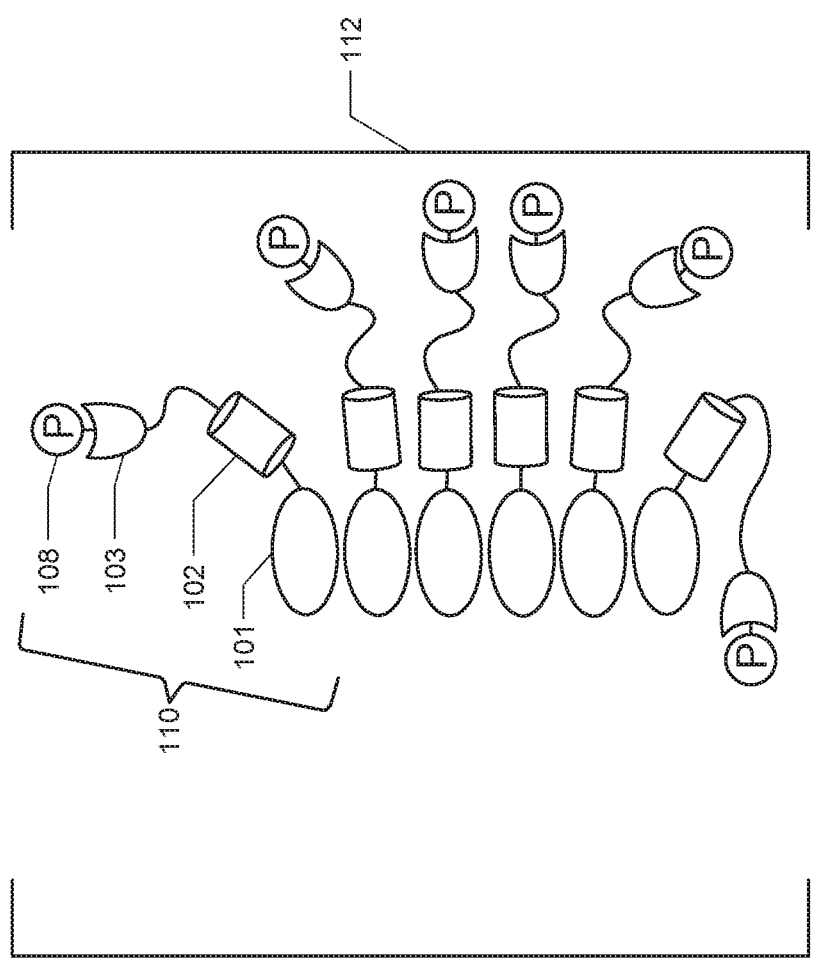
FIG. 1B depicts a first hexamer reporter oligomer 112 formed of six monomers 110 by the spontaneous oligimerization the first coiled coil subunit 101. The oligomeric reporter comprises six copies of the first interacting protein 103 and six copies of the fluorescent protein 102. In the presence of the kinase PKA, the first interacting protein has become phosphorylated with phosphoryl groups 108 rendering it active, in that it can react with the second interacting protein 106.
Figure 1C:
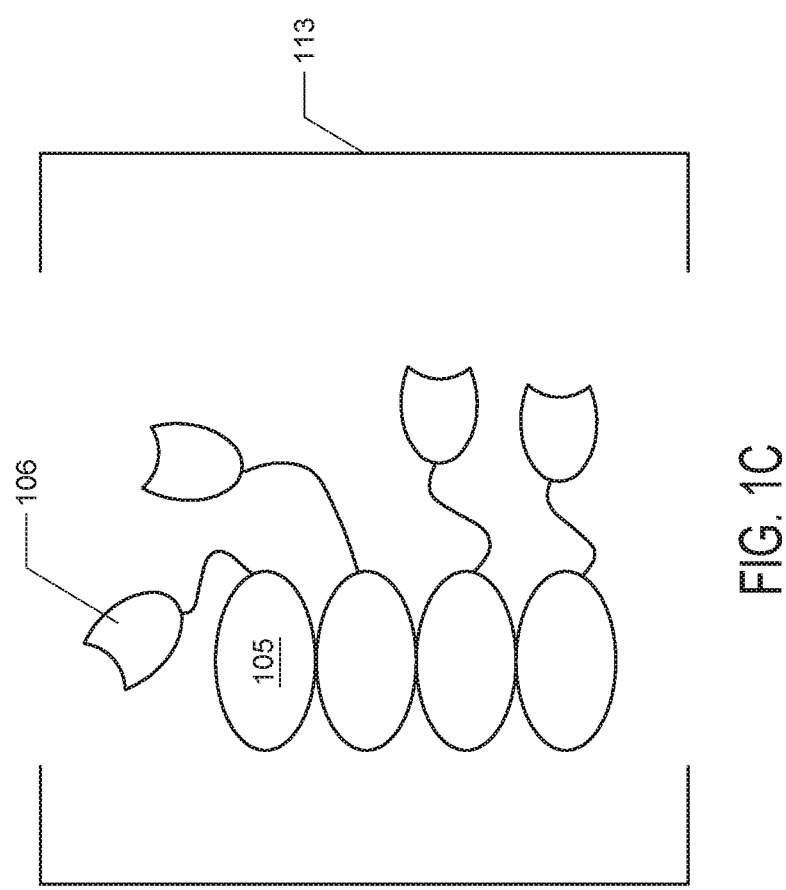
FIG. 1C.

Fusion Proteins. The monomers of the invention are conveniently expressed as fusion proteins, i.e. expressed in-line as a single polypeptide sequence. Coiled coil subunits may be joined to other elements at the coiled coil subunits' carboxy and/or amino terminus. Typically, the fluorescent proteins, when present, will be expressed between the coiled coil subunit and the interacting protein, for example, as in FIG. 1B, but any arrangement of the elements may be used. The elements of the fusion protein may be joined end-to-end, or may comprise intervening linker sequences to afford conformational flexibility. For example, the linker may comprise one or more repeats of the flexible linker sequence SEQ ID NO: 16, GGGGS. Linkers may be, for example, 10-40 amino acids in length.

It will be understood that the monomer fusion proteins may include additional elements, including additional interacting proteins, nuclear localization signals, or other moieties for targeting the reporter proteins to cellular compartments or organelles.

The two monomers of the invention may be expressed separately, as two distinct expression products and may be coded for by separate nucleic acid sequences. Conveniently, however, the two monomers may be expressed from a single DNA sequence. In one embodiment, the first and second monomers are encoded by a single nucleotide sequence, separated by an intervening "self-cleaving" peptide sequence, as known in the art. For example, the self-cleaving peptide sequence may comprise a 2A sequence, for example, a 2A sequence selected from the group consisting of P2A, F2A, T2A, or E2A. Upon translation of the single mRNA coding for both monomers, the self-cleavable moiety splits the protein, resulting in the formation of two separate monomer fusion proteins. The use of such a construct enables expression of the reporter system from a single transformation event with a polycistronic vector. In the typical implementation, the monomers are expressed in a 1:1 ratio, however different stoichiometries may be used.

In one embodiment, the scope of the invention encompasses a nucleic acid construct which codes for the monomers of the invention. In one embodiment, the nucleic acid comprises an expression vector, a transformation vector, a plasmid, or DNA integrated into the genome of a host organism. In one embodiment, the nucleic acid construct of the invention further comprises a promoter sequence, for example, wherein the promoter may be constitutive, organ specific, developmentally regulated, or inducible.

In one embodiment, the scope of the invention encompasses cells engineered to express the monomers of the invention. In one embodiment, the scope of the invention encompasses organisms engineered to express monomers of the invention. The cells and organisms may be engineered to express the reporter system of the invention by any means known in the art, for example, by viral vectors, electroporation, vacuum infiltration, silicon carbide whisker, laser microbeams, ultrasound, shock wave-mediated genetic transformation, or biolistic techniques. The cells or organisms may be prokaryotic or eukaryotic species. In one embodiment, the cells or organisms are selected from the group consisting of bacteria, yeast, fungi, plants, and animals, including test animals or humans, for example, nematodes, mice, rats, zebrafish, *Drosophila*, or any other species, particularly small animal species amenable to imaging.

Expression and Formation of the Reporter System Oligomers. Upon expression, the monomers will accumulate and will spontaneously form coiled coil homo-oligomers, the oligomers having a valency determined by the coiled coil subunit protein sequence. Dimers, trimers, tetramers, pentamers, hexamers, heptamers, and higher order coiled coil conformations may be formed. For example, wherein Hotag3 (SEQ ID NO: 3) is utilized as one of the subunits, hexamers of the functionalized Hotag3 protein sequences will form. Wherein Hotag6 (SEQ ID NO: 6) is utilized, tetramers of the functionalized Hotag6 protein sequence will form.

The reporter proteins of the invention will effectively form droplets across a range of concentrations. For example, reporter protein concentrations of 1-100 µM, for example, in the range of 2-10 µM may be used. Advantageously, signal generation is stable across a broad range of reporter protein concentrations in the cell. Furthermore, the homo-oligomers were not found to be toxic or disruptive to normal cellular function.

While the system of the invention is conveniently used in living cells, it will be understood that the reporter elements may be used in in vitro assays as well.

Activation, Droplet Formation, and Quantification of Target Processes. Upon formation of the multivalent homo-oligomers of the reporter system, the occurrence of the targeted protein-protein interaction will result in a readily measurable signal. The protein-protein interaction may be constitutive, or may be induced, for example, being induced by a chemical, biological, or developmental stimulus or treatment. If one (or both) of the interacting proteins is activable, the protein-protein interaction may be initiated by an activating treatment or stimulus which converts the activable protein from the inactive to the active form. In one embodiment, the activating treatment is the administration of a composition of matter to the cells. The composition of matter may comprise a drug, small molecule, biological molecule (e.g. protein, transcription factor, enzyme, antibody, inhibitor protein, nucleic acid, etc.).

Figure 1D:
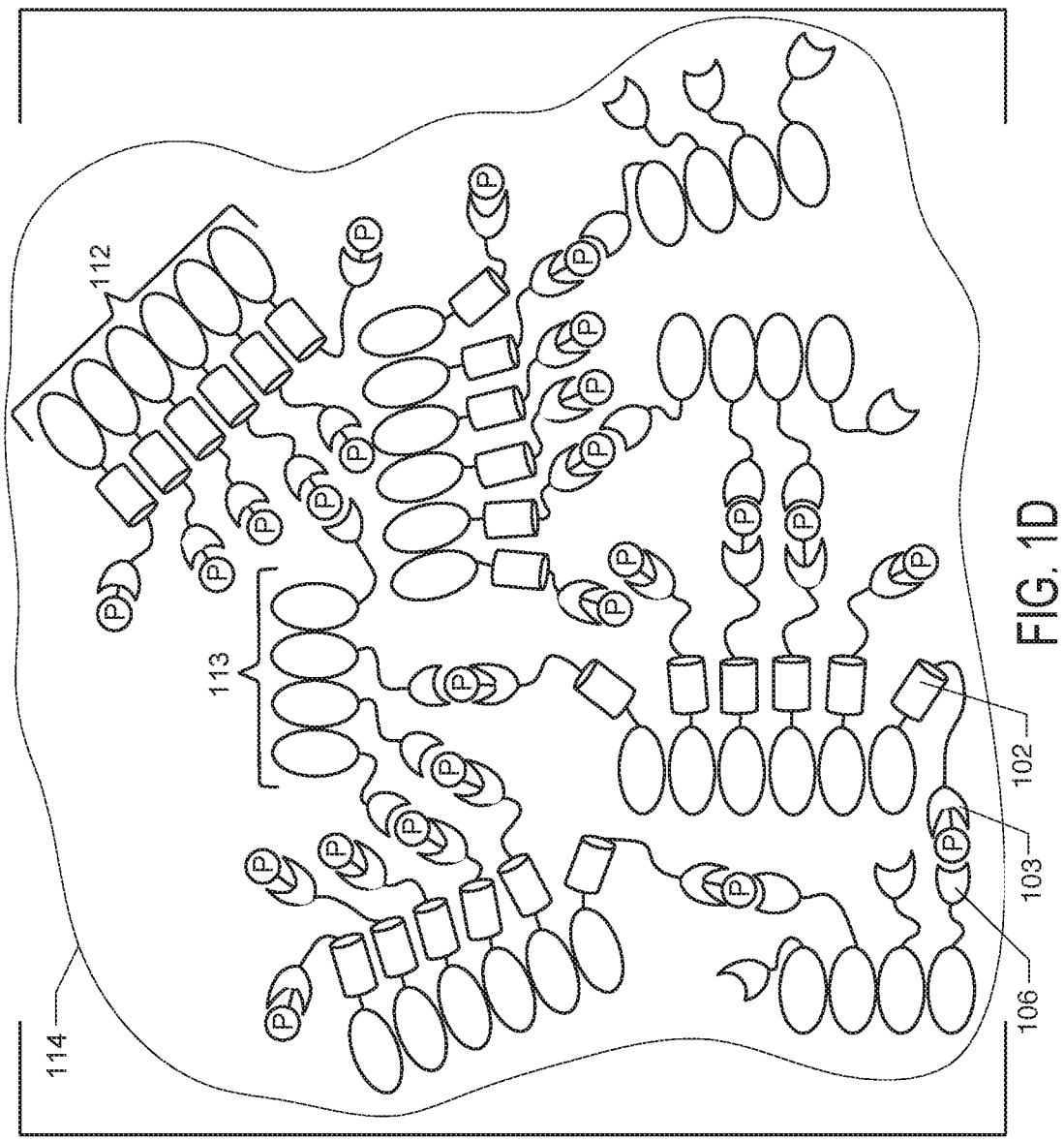
FIG. 1D.
Figure 2A:
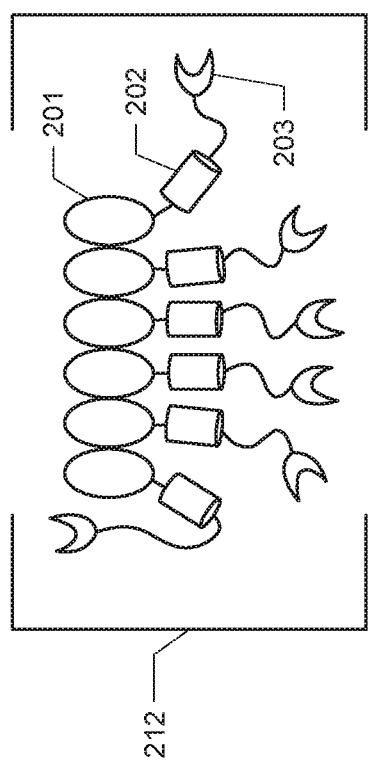
FIGS. 2A, 2B, 2C, and 2D.
Figure 2B:
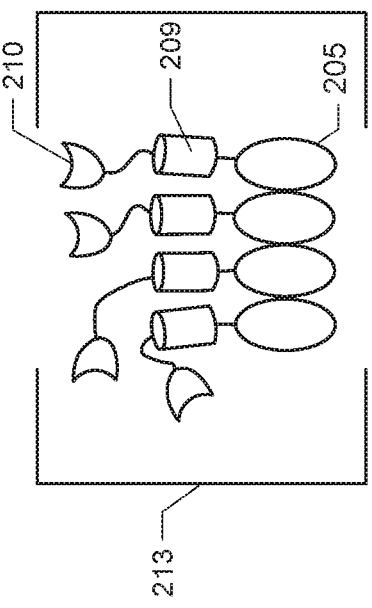
Figure 2C:
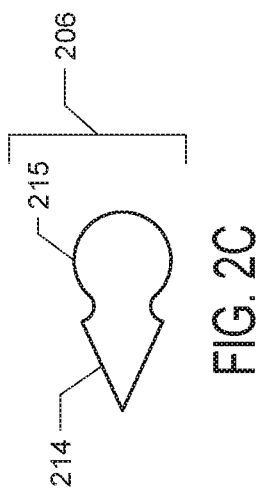
Figure 2D:
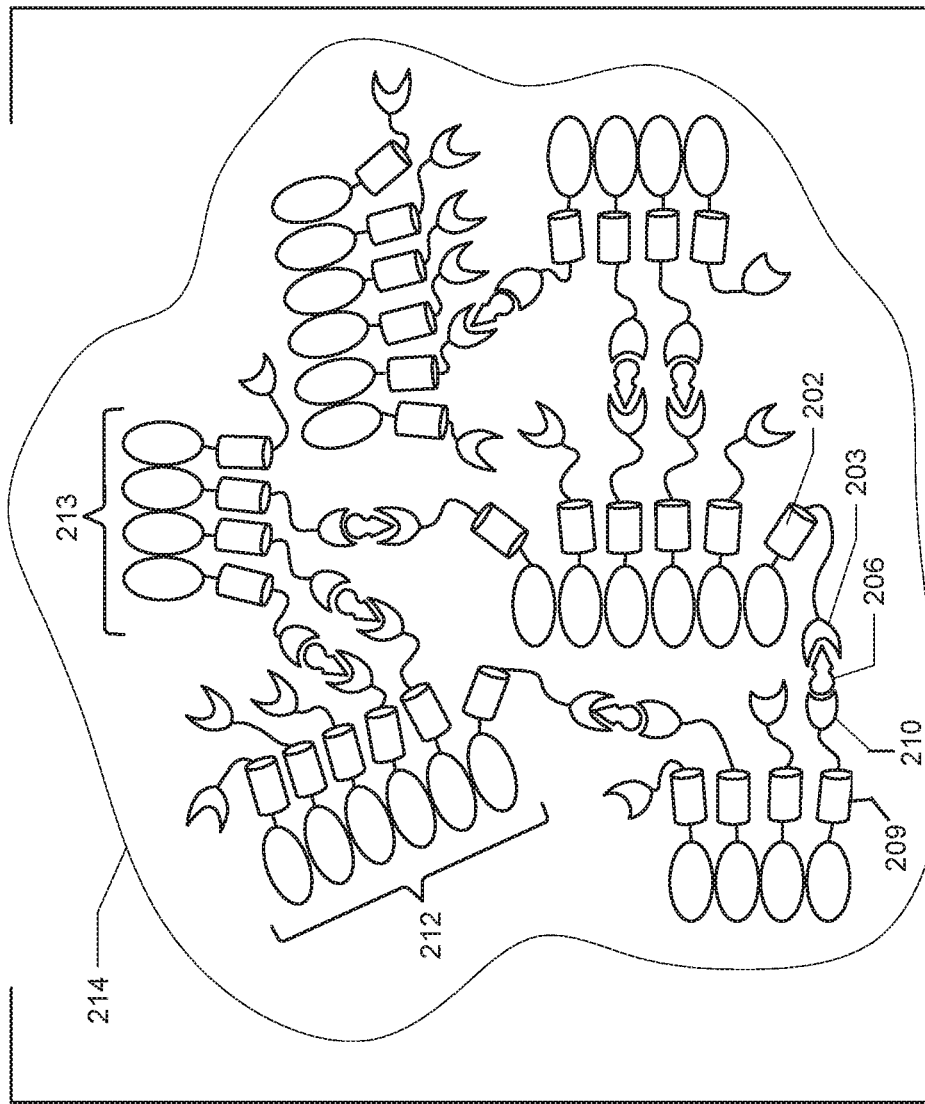
Figure 3A:
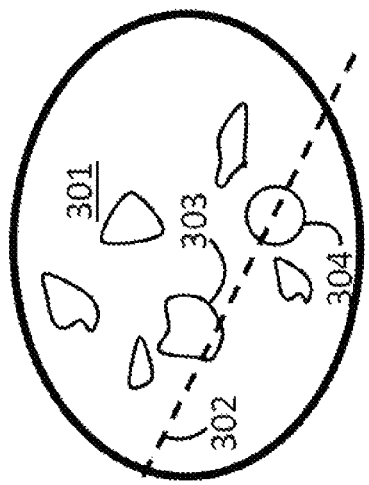
FIGS. 3A, 3B, 3C, 3D, 3E, and 3F.
Figure 3B:
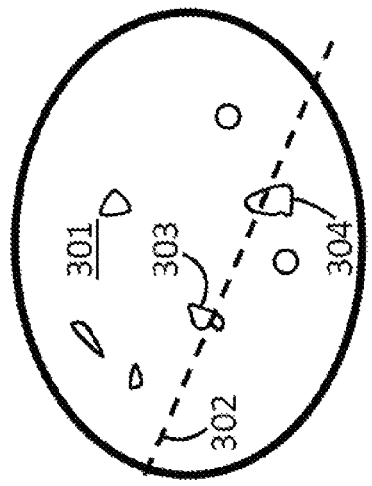
Figure 3C:
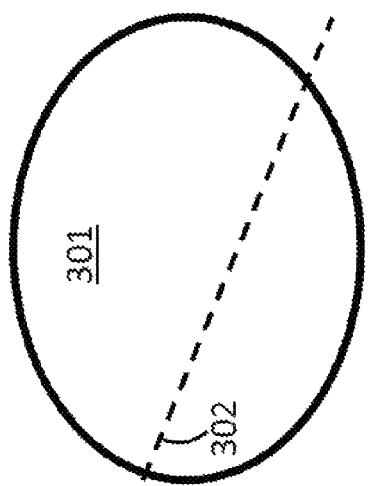
Figure 3D:
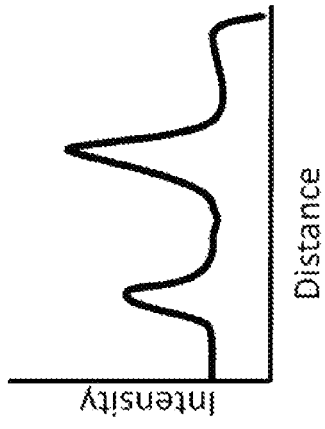
Figure 3E:
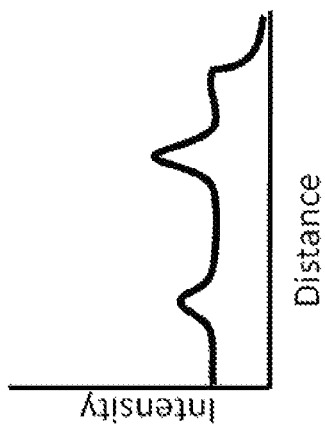
Figure 3F:
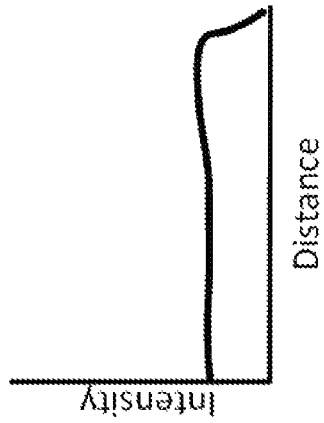

When the selected protein-protein interaction occurs, the interacting proteins of the complementary oligomers will bind, connect, or otherwise associate. For example, as depicted in FIG. 1D, the interacting proteins present on each homo-oligomer can form connections with complementary interacting proteins on two or more complementary oligomers. The resulting aggregation or network of cross-linked elements creates a localized, extremely high concentration of homo-oligomers. With sufficient numbers of interacting molecules, this results in a demixing, or phase shift that forms a discreet, membraneless organelle similar to the droplets or granules formed by native multivalent proteins. For example, aggregations of thousands to millions of oligomers may occur, resulting in microdroplets of ~0.1-1 microns in diameter.

Within these droplets, the fluorescent proteins (or other reporters) are highly concentrated, creating a bright and distinct signal. When imaged by a modality compatible with the selected fluorescent protein, i.e. at the appropriate excitation wavelengths, the droplets will appear as distinct punctae, speckles, or islands of bright signal. Typically, the reporter system responds rapidly to the onset of the protein-protein reaction, with rapid formation of punctae within second to minutes.

The large fluorescent signal and high brightness in these discrete punctae is readily detected, even in whole animals. Accordingly, the reporter system of the invention is amenable to use in live, intact animals for in vivo detection of protein-protein interactions. Fluorescent protein signals may be analyzed with techniques known in the art. Quantitative imaging of fluorescent proteins is readily accomplished with a variety of techniques, including, but not limited to widefield, confocal, and multiphoton microscopy, with microscope equipment and methods to be selected as appropriate for selected fluorescent reporters. Fluorescence images may be acquired with exposure times appropriate for the selected fluorescent protein, for example 50 ms for EGFP, 100 ms for mCherry, and 200 ms for mIFP. Time-lapse photography, for example, at intervals of 1-20 seconds, for example, 10 seconds, may be used over time intervals of minutes to hours. Reporter concentration may be estimated by methods known in the art, for example, as described in Shin et al., (2016). Spatiotemporal Control of Intracellular Phase Transitions Using Light-Activated optoDroplets. Cell 168, 159-171.

With bright signal and readily imaged droplets, the system provides a facile qualitative analysis based on raw images, without the need for additional quantitative data analysis. Alternatively, the system may act as a quantitative indicator of the selected-protein protein interaction, as the abundance of punctae and the level of fluorescent signals are proportional to the scale of the protein-protein interaction. Signal may be quantified by any appropriate technique. In one embodiment, the sum of fluorescent droplets' pixel intensity divided by the sum of the cell's overall pixel intensity is utilized as the measure of signal. Other measures of signal include histograms of signal intensity in a scan taken along a line selected across the width of the cell, wherein strong peaks are indicative of localized islands of signal and the area under the line is quantitative for signal. An exemplary histogram quantification is depicted in FIGS. 3A, 3B, 3C, 3D, 3E, and 3F.

In an alternative embodiment, the assay is performed in a "signal-off" configuration. In this implementation, the monomers, as expressed, will form homo-oligomers that coalesce into a cross-linked network as the two protein partners interact, forming readily visualized punctae. Upon occurrence of a stimulus or application of a treatment that disrupts the protein-protein interaction, the multivalent interactions are inhibited and the signal is reduced or abolished as the aggregated oligomers are dispersed.

Protein-protein Interactions. The reporters and associated methods of the invention may be utilized for the observation and measurement of any selected protein-protein interaction. Exemplary protein-protein interactions include enzyme-substrate interactions, receptor-ligand interactions, and other protein-protein interaction known in the art. The interactions may comprise, for example, constitutive interactions, small molecule-induced interactions, small molecule-inhibited interactions, and biologically induced interactions. For instance, immunomodulatory drugs (e.g. thalidomide or lenolidomide) induce interaction between cereblon and ikaros or GSPT1, leading to droplet formation. The GTP-bound small GTPases (e.g. Kras) are active and can bind their effector proteins (e.g. Raf1), which leads to droplet formation. Other exemplary protein-protein interactions include SKP2 (activable) interactions with SKP1, P53 (activable) interactions with Mdm2, RhoA (activable upon GTP binding) and rhotekin, CDC42 (activable upon GTP binding) and WASP, and Rac1 (activable upon GTP binding) and PAK1.

In one embodiment, the method of the invention is directed to the measurement of enzyme activity by a selected enzyme. In this implementation, the first interacting protein comprises a substrate for the selected enzyme, wherein the action of the enzyme activates the first interacting protein such that it may interact with the second interacting protein. Thus, droplet formation is driven by and proportional to the activity of the selected enzyme by its activation of the first interacting species.

In one implementation, the reporter system of the invention comprises a kinase reporter system. In this configuration, the first interacting protein is a protein that will only interact with the second interacting protein when phosphorylated. Therefore, droplet formation is dependent upon and proportional to activity of the selected kinase. For example, in the exemplary embodiment described in Example 1 and in FIG. 1A-1D, the first interacting protein is a consensus peptide sequence that is specifically phosphorylated by the kinase PKA, comprising SEQ ID NO: 17, LRRATLVD, and the second interacting protein is Forkhead-associated domain 1 (FHA1), wherein the first interacting protein must be phosphorylated by PKA for it to interact with FHA1. In such a system, SEQ ID NO: 17 is the activable species, PKA activity is the activator, and droplet formation is proportional to PKA activity.

Kinase reporter system may may be configured to detect the activity of kinases such as c-Jun N-terminal kinases (JNK); Protein Kinase A, Protein Kinase B (PKB, also known as Akt); Protein Kinase C (PKC); Ataxia telangiectasia mutated kinase (ATM); AMP-activated protein kinase (AMPK); Abl kinase; Protein kinase D (PKD); Proto-oncogene tyrosine-protein kinase Src; Focal adhesion kinase (FAK), Cyclin-dependent kinases, and extracellular related signaling kinases (ERK). It will be appreciated by those skilled in the art that the detection of kinase activity is not limited to the foregoing list, and further includes, for example, kinases found in eukaryotic, archaeal, and bacterial cells.

PROTAC Assays. In certain implementations, the reporters and methods of the invention may be employed in testing the efficacy of proteolysis targeting chimeras (PROTACs). PROTAC is a chimeric molecule that consists of two ligands joined by a linker moiety: the first ligand being a sequence that binds to an E3 ligase, and the second ligand being a sequence that binds a target protein. PROTAC is thus a bifunctional molecule that brings the target protein in spatial proximity to the E3 ligase, triggering ubiquitination and proteosomal degradation. Over the past two decades, PROTAC has emerged as a powerful tool for targeted degradation of endogenous proteins including "undruggable" targets. Structural factors are very important in determining PROTAC efficacy and selectivity. Efficient and selective degradation of the target protein depends on stability of the ternary complex (E3 ligase-PROTAC-target protein), which is affected by the topology of the PROTAC construct, including length and composition of the linker. Thus, rapid and quantitative detection of PROTAC-induced ternary complex in live cells would provide a valuable tool for identification and optimization of PROTACs.

An ideal assay to detect PROTAC-induced protein-protein interactions should have large dynamic range (fluorescence change), high brightness and sensitivity, rapid and reversible kinetics, be quantitative, and be applicable to live cells so that protein-protein interactions of the ternary complex may be observed under in vivo conditions. Although several protein-protein interaction assays exist, none of them has been demonstrated in quantitative, fast and robust detection of PROTAC-induced protein-protein interactions in live cells. Accordingly, the reporters and methods of the invention have been adapted to the testing of PROTAC components for the development and optimization of PROTAC designs.

In one embodiment, the scope of the invention encompasses a first and second reporter monomer, wherein the first interacting protein is a selected target protein and wherein the second interacting protein comprises an E3 ubiquitin ligase. The E3 ligase of the system may comprise any E3 ligase or functionally equivalent protein known in the art, or a portion thereof that is capable of binding a selected E3 ligase recognition element. These monomers are expressed in the cell and form homo-oligomers.

The reporter system is used in combination with a compatible PROTAC construct. The PROTAC construct will comprise: a target-protein binding ligand capable of selectively binding the selected target protein (first interacting protein); an intervening linker sequence; and an E3 ligase recognition domain capable of selectively binding the E3 ligase comprising the second interacting protein. The E3 ligase recognition domain may comprise any known in the art, for example: a phosphopeptide of sequence SEQ ID NO: 18, DRHDSGLDSM, wherein the serines are phosphorylated; a peptide of sequence SEQ ID NO: 19, ALAPYIP; or other ligands to recruit E3 ubiquitin ligases, for example, as described in Gu et al., 2018, "PROTACs: An Emerging Targeting Technique for Protein Degradation in Drug Discovery," BioEssays 2018, 40, 1700247.

In the assay method of the invention, the PROTAC construct is applied exogenously to or expressed in cells expressing the reporter system, during or before the measurement step. For example, the PROTAC construct may be applied at concentrations ranging from 1 nM to 5 µM. Upon addition, binding of the first interacting protein to the target recognition moiety of the PROTAC sequence will occur and binding of the second interacting protein (E3 ligase) to the E3 ligase recognition element of the PROTAC construct will occur, for example, as depicted in FIGS. 2A, 2B, 2C, and 2D. The PROTAC will thus form a bridge between the first and second interacting proteins and will drive the formation of cross-linked oligomer networks and droplet formation. The kinetics and magnitude of the signal are determined by the efficacy of PROTAC construct binding to both the target protein and E3 ligase. Thus, the system provides the art with an effective means of measuring PROTAC performance and comparing different PROTAC designs.

The PROTAC construct may be configured as known in the art. Exemplary PROTAC constructs include those described in Salami and Crews, 2017, "Waste Disposal—an attractive Strategy for Cancer Therapy, Science 355, 1163-1167.

Exemplary Embodiments. The following are exemplary implementations and configurations of the invention.

In certain embodiments, the scope of the invention encompasses a pair of reporter monomers. In one embodiment, the pair of reporter monomers comprises
a first monomer comprising a fusion protein, wherein the fusion protein comprises: a first coiled coil subunit that will spontaneously form a homo-oligomer with other coiled coil subunits of the same sequence; and a first interacting protein; and
a second monomer comprising a fusion protein, wherein the second fusion protein comprises: a second coiled coil subunit that will spontaneously form a homo-oligomer with other coiled coil subunits of the same sequence; and a second interacting protein;
wherein the first and second coiled coil subunits comprise different sequences;
wherein the first interacting protein and second interacting protein comprise the members of an interacting protein pair;
wherein the first fusion protein, the second fusion protein, or both the first and second fusion proteins further comprises one or more fluorescent proteins or other reporter moieties.

In one embodiment, the first coiled coil subunit and the second coiled coil subunit are selected from the group consisting of SEQ ID NO: 1-SEQ ID NO: 15, or variants thereof. In one embodiment, the first and second coiled coil subunits are SEQ ID NO: 3 (HoTag3) and SEQ ID NO: 6 (HoTag6), or variants thereof. In one embodiment, first coiled coil subunit and the second coiled coil subunit are less than 45 amino acids in length. In one embodiment, first coiled coil subunit and the second coiled coil subunit are 20-35 amino acids in length.

In one embodiment, the first interacting protein or the second interacting protein is activable. In various embodiments, the activable protein is activated by phosphorylation, dephosphorylation, methylation, glycosylation, oxidation, reduction, binding of co-factors, displacement of ligands, or a conformational change. In one embodiment, the activation is achieved directly by an activating species. In one embodiment, the activating species is an enzyme. In one embodiment, the enzyme is a kinase. In one embodiment the enzyme is a phosphatase. In one embodiment, activation occurs as a result of changes in the microenvironment of the cells wherein the activable protein is expressed, e.g. changes in pH, oxygenation, redox balance, or presence or concentration of selected ions.

In one embodiment, the first interacting protein and the second interacting protein comprise a polypeptide selected from the group consisting of a whole protein, a protein fragment, and a protein domain. In one embodiment, the first interacting protein comprises the binding domain for a target species, wherein the target species interacts with the second interacting protein. In one embodiment, the first interacting protein and the second interacting protein of the pair of fusion proteins comprise an enzyme and a substrate. In one embodiment, the first interacting protein and the second interacting protein of the pair of fusion proteins comprise a receptor and a ligand.

In one embodiment, the first interacting protein comprises an E3 ubiquitin ligase and the second interacting protein comprises the target of a PROTAC construct.

In one embodiment, the one or more fluorescent proteins is selected from the group consisting of GFP, EGFP, a GFP variant, mNeon, mOrange, mKO2, tdTomato, mCherry, FusionRed, mApple, IFP2.0, and mIFP In one embodiment, the first and the second monomers are expressed as a single fusion protein comprising a self-cleaving moiety disposed between the first and the second fusion proteins. In one embodiment, the self-cleaving sequence is a 2A sequence, for example, a 2A sequence selected from the group consisting of P2A, F2A, T2A, or E2A.

In one embodiment, the scope of the invention encompasses a nucleic acid construct coding for the first monomer, the second monomer, or both the first and the second monomers. In one embodiment, the first and second monomers are expressed in a cell. In one embodiment, the cell is a prokaryotic cell. In one embodiment, the cell is a eukaryotic cell. In one embodiment, the first and second monomers are expressed in a living whole organism. In one embodiment, the organism is an animal.

In one embodiment, the scope of the invention encompasses a homo-oligomer comprising a homo-oligomer of the first monomer. In one embodiment, the invention encompasses a homo-oligomer comprising a homo-oligomer of the second monomer. In one embodiment, the invention encompasses a cell comprising homo-oligomers of first and second monomers, formed by the expression of the monomers in the cell.

In one embodiment, the scope of the invention encompasses methods of detecting a protein-protein interaction in a cell by the use of the monomers of the invention. In one embodiment, detection of the protein-protein interaction encompasses observing the occurrence, of, measuring the kinetics of, or quantifying the degree of the selected protein-protein interaction. In one embodiment, the method comprises a method of detecting the interaction of a first interacting protein and a second interacting protein in a cell, comprising the steps of:
expressing a first monomer in the cell, wherein the first monomer is a fusion protein, wherein the fusion protein comprises: a first coiled coil subunit that will spontaneously form a homo-oligomer with other coiled coil subunits of the same sequence; and the first interacting protein; and
expressing a second monomer in the cell, wherein the second monomer is a fusion protein, wherein the fusion protein comprises: a second coiled coil subunit that will spontaneously form a homo-oligomer with other coiled coil subunits of the same sequence; and the second interacting protein;
wherein the first and second coiled coil subunits comprise different sequences;
wherein the first monomer, the second monomer, or both the first and second monomers further comprises one or more fluorescent proteins or other reporter moieties; and
by methods of detecting the one or more fluorescent protein or other reporter moieties, observing the cell for the formation of localized punctae comprising phase-shifted droplets of concentrated aggregates of homo-oligomers of the first monomer and homo-oligomers of the second monomer, wherein the formation of the aggregations of homo-oligomers is driven by the interaction of the first interacting protein and the second interacting protein.

In one embodiment, the observation is by fluorescent microscopy. In one embodiment, the observation is by time-lapse photography for a selected interval of time.

In one embodiment, the method comprises the additional step, performed prior to or during the observation step, of subjecting the cells to a treatment or stimulus which modulates the protein-protein interaction. In one embodiment, the first and/or second interacting proteins comprises an activable protein and the stimulus or treatment activates the activable protein such that it can interact with the complementary interacting protein. In one embodiment, the stimulus or treatment deactivates the activable protein such that its interaction with the complementary interacting protein is inhibited. In one embodiment, the stimulus or treatment is the administration of a composition of matter. In one embodiment, the composition of matter is a drug or a biological molecule.

In one embodiment, in the method of the invention, the first coiled coil subunit and the second coiled coil subunits are selected from the group consisting of SEQ ID NO: 1-SEQ ID NO: 15. In one embodiment, in the method of the invention, the first and second coiled coil subunits are SEQ ID NO: 3 (HoTag3) and SEQ ID NO: 6 (HoTag6).

In one embodiment, in the method of the invention, the one or more fluorescent proteins or other reporter moieties are present on the first fusion protein, are present on the second fusion protein, or are present on both fusion proteins. In one embodiment, the one or more fluorescent proteins is selected from the group consisting of GFP, EGFP, a GFP variant, mNeon, mOrange, mKO2, tdTomato, mCherry, FusionRed, mApple, IFP2.0, and mIFP In one embodiment, in the method of the invention, the first interacting protein and the second interacting protein comprise a polypeptide selected from the group consisting of a whole protein, a protein fragment, and a protein domain. In one embodiment, the first interacting protein and second interacting proteins are 10-10,000 amino acids in length.

In one embodiment, the method of the invention is directed to the measurement of enzyme activity by a selected enzyme. In this implementation, the first interacting protein comprises a substrate for the selected enzyme, wherein the action of the enzyme activates the first interacting protein such that it may interact with the second interacting protein. In one embodiment, the selected enzyme is a kinase and the first interacting protein is a protein that will only interact with the second interacting protein when phosphorylated.

In one embodiment, the method of the invention encompasses a method of evaluating the performance of a PROTAC construct. In this implementation, the first interacting protein comprises an E3 ubiquitin ligase and the second member of the interacting protein pair comprises the target protein;
and wherein the PROTAC construct is applied to or expressed in the cells prior to or during the observation step;
wherein the PROTAC comprises an E3 ligase binding moiety and a target protein binding moiety; and
wherein binding of the first interacting protein (E3 ligase) to the E3 ligase binding moiety of the PROTAC construct and binding of the second interacting protein (target protein) to the target binding moiety of the PROTAC construct drives the formation of aggregates of homo-oligomers and phase shifted droplets.

EXAMPLES

Example 1, Visualizing Dynamics of Cell Signaling In Vivo with a Phase Separation-Based Kinase Reporter To robustly image dynamic kinase activity in vivo, reporters were developed that, upon kinase activation, phase separate and form highly concentrated droplets. The well characterized FKBP and Frb were selected as an inducible protein-protein interaction system since their interaction can be robustly induced by rapamycin. Seven coiled coils previously characterized in previous protein de novo design studies, HOTag1 to HOTag7 (SEQ ID NO: 1-7). To achieve high multivalency, coiled coils that have high stoichiometry, forming tetramer, pentamer, hexamer, and heptamers were selected.

Characterization of the seven HOTags using FKBP and Frb PPI pair in human embryonic kidney 293 (HEK293) cells showed that HOTag3 and HOTag6 were most robust in driving rapamycin-inducible protein droplet formation over a wide range of protein concentration. HOTag3 and 6 were highly soluble when fused to FKBP and EGFP fusion. To examine kinetics of the EGFP phase separation upon rapamycin-induced PPI in living cells, time-lapse fluorescence imaging was performed, which revealed that fluorescent droplets formed within two minutes upon rapamycin addition. Since this includes the time necessary for the rapamycin to diffuse through cell membrane, the kinetics of droplet formation is likely faster. The fluorescent droplets could be qualitatively and easily identified because of their brightness and signal pattern. They could also be quantified and plotted as a fluorescent histogram at the pixel level, which showed high brightness and large signal. Since the hexameric HOTag3 and the tetrameric HOTag6 can robustly drive protein phase separation upon protein interaction, the HOTag3/6 pair was selected for use as kinase reporters.

Protein phase separation and formation of droplets can be attributed to two main factors: PPI and multivalency. In the system tested here, rapamycin induced PPI between FKBP and Frb, whereas multivalency is introduced by the HOTags. Rapamycin and HOTags induced multivalent PPIs that drive protein phase separation and formation of EGFP droplets; addition of rapamycin induced protein separation into two phases—a dilute phase and a concentrated phase. The high-concentration phase is the protein condensate or droplet. At equilibrium state, the chemical potential of the dilute and condensed phases are equivalent for both proteins and solvent. The results showed that the paired HOTag3 and HOTag6 were excellent multivalent tags capable of driving protein phase separation upon protein-protein interaction over a large range of protein concentration.

To determine whether HOTag3 and HOTag6 can be used to design a separation of phases-based activity reporter of kinase (SPARK), a construct was generated for detecting protein kinase A (PKA) activity. PKA is an important mediator of G protein-coupled receptor (GPCR) signaling, but the signal of current PKA reporters, including both FRET- and translocation-based reporters, is small, with ~30% ratio change of the fluorescence, for example as demonstrated in Regot et al., (2014). High-Sensitivity Measurements of Multiple Kinase Activities in Live Single Cells. Cell 157, 1724-1734 and Zhang et al., (2005). Insulin disrupts beta-adrenergic signaling to protein kinase A in adipocytes. Nature 437, 569-573.

To design a SPARK-based PKA, reporter (named PKA-SPARK), a consensus peptide sequence was utilized that is specifically phosphorylated by PKA, as described in Durocher et al., (2000). The molecular basis of FHA domain: phosphopeptide binding specificity and implications for phospho-dependent signaling mechanisms. Mol Cell 6, 1169-1182. To introduce PKA activity-dependent PPI, fork-head-associated domain 1 (FHA1) was sued, which is a phosphothreonine binding domain. Both motifs have been successfully used in the FRET-based PKA reporters of Zhang et al. The PKA substrate sequence was fused to EGFP followed by HOTag3, and FHA1 was fused to HOTag6. These two fusion sequences were connected by a "self-cleaving" 2A sequence. The rationale was that substrate and the FHA1 would induce PKA activity-dependent protein-protein interaction, the two HOTags introduce multivalency; and upon PKA activation, multivalent protein-protein interactions would be induced, leading to phase separation and formation of EGFP droplets.

To test the construct, the β-adrenergic agonist isoprenaline was added to HEK293 cells that endogenously express β-adrenergic receptors (βAR). βAR activation induces GDP for GTP exchange in the heterotrimeric G protein Gs, and GTP-bound Gαs activates adenylyl cyclase (AC), which converts ATP into cAMP that activates PKA. Upon addition of the βAR agonist, fluorescent droplets formed in the reporter-expressing HEK293 cells. In contrast, pre-incubation with the PKA inhibitor H89 abolished isoprenaline-induced droplet formation. These results suggest that PKA activation induced EGFP phase separation. In order to confirm that the phase separation results from phosphorylation of PKA-SPARK at the expected threonine residue, we changed the threonine to alanine in the PKA substrate sequence. This mutant PKA-SPARK did not form fluorescent droplets in cells stimulated with isoprenaline. These results suggest that phosphorylation of the single threonine is responsible for the PKA activity-dependent phase separation of the reporter, Lastly, removal of either HOTag3 or HOTag6 or both abolished droplet formation upon isoprenaline stimulation, indicating that both HOTags are required for droplet formation. The data thus suggests that PKA activity-triggered multivalent interaction between FHA1-HOTag6 and the PKA substrate peptide-EGFP-HOTag3 lead to EGFP phase separation.

Next it was tested whether phase separation of the reporter is reversible, i.e. whether the EGFP droplets would disassemble or dissolve when PKA is inactivated. Cells were pre-incubated with isoprenaline to induce phase separation, then isoprenaline was removed and H89 added to inactivate PKA. The EGFP droplets disassembled rapidly, which is consistent with previous studies that used a FRET PKA reporter and reported that H89 inactivates isoprenaline-induced PKA activation. As a control, the EGFP droplets were stable over time in the cells with removal of isoprenaline but addition of medium without H89. The reversibility of the EGFP droplets suggests that the droplets are accessible to protein phosphatases, which is consistent with previous studies that protein droplets not only contain "scaffold" proteins responsible for droplet's formation, but also contain "client" proteins, which interact with "scaffold" proteins but are not required for the droplet's formation. To examine whether PKA-SPARK could quantitatively measure the droplets' disassembly over time after PKA inhibition, we defined "SPARK signal" as the sum of fluorescent droplets' pixel intensity divided by sum of cells' pixel intensity. Upon addition of H89, the SPARK signal decreased over time. In contrast, for the control the SPARK signal remained constant over time. These results suggest that SPARK signal quantitatively described droplets' disassembly upon inhibition of PKA.

Time-lapse fluorescence imaging of PKA-SPARK was performed at 10 seconds per frame. Fluorescent droplets formed after addition of isoprenaline, and the SPARK signal increased over time. PKA activation upon addition of isoprenaline was confirmed by AKAR2 reporter. Small droplets of PKA-SPARK were detected as early as at 20 seconds upon addition of isoprenaline. The quick activation of PKA is consistent with rapid activation of the βAR-cAMP-PKA pathway. The small droplets grew quickly and coalesced into large and intensively fluorescent droplets, which were up to 10-fold brighter than the cellular fluorescence before PKA activation. In contrast, the prior art PKA-KTR reporter showed much smaller fluorescence change. Therefore, PKA-SPARK achieves up to 10-fold fluorescence increase, compared to prior art AKAR2 and PKA-KTR reporters, which have ~10% and ~30% fluorescence ratio change, respectively. The results demonstrated that PKA-SPARK achieves large fluorescence change, high brightness and fast kinetics for reporting kinase activity. The results also verified that PKA-SPARK could detect PKA activity over a wide range of reporter expression. Lastly the concentration of PKA-SPARK (2-10 μM) appeared to have no effect on kinetics of droplet assembly and disassembly.

The results with PKA-SPARK demonstrate that the intensive fluorescence and simple signal pattern of the reporters of the invention allow easy and straightforward examination of PKA signaling in a qualitative way, based on raw images with no requirement of quantitative data analysis. This is in contrast to the previous PKA reporters including AKAR2 and PKA-KTR, wherein the small fluorescence change makes them difficult to identify PKA activity without quantitative data analysis.

In additional experiments, PKA was activated via the G-coupled GPCR βAR. Isoprenaline was added to activate endogenous βARs in HEK293 cells. EGFP droplets formed and persisted for at least 3 hrs, suggesting sustained PKA activity. Pre-incubation of cells with the βAR antagonist carvedilol abolished the sustained PKA-SPARK signals induced by isoprenaline.

To determine whether the SPARK design generalizes, the highly conserved kinase ERK was utilized in a second pair of reporter fusion proteins. To design a SPARK-based ERK reporter (ERK-SPARK), the ERK activity-sensing motifs that were used for previous FRET-based ERK reporters were employed. One of the ERK activity-sensing motifs is a phosphopeptide sequence from Cdc25C, followed by an ERK-specific docking site that determines substrate specificity. The companion fragment is a WW domain that binds the phosphorylated substrate. The ERK substrate sequence was fused to EGFP followed by HOTag3, and the WW domain was fused to EGFP followed by HOTag6. The two fusions were connected by a "self-cleaving" 2A sequence. The pair of reporter fusion proteins was expressed in HEK293 cells exposed to epidermal growth factor (EGF). EGF binds the EGF receptor, resulting in ERK activation. As expected, EGFP droplets formed upon addition of EGF. In contrast, cells expressing a reporter with a mutated CDC25C peptide fragment that is phosphorylated by ERK did not exhibit formation of EGFP droplets after EGF treatment. Because the ERK docking site was previously shown to be critical for ERK recognition and binding to substrate, a reporter lacking the 4-amino-acid docking site was generated. As expected, this mutated reporter did not show phase separation upon addition of EGF. Lastly, removal of either HOTag3 or HOTag6 or both abolished droplet formation upon EGF stimulation, indicating that both HOTags are required for droplet formation. By time-lapse imaging transient ERK activation was observed upon addition of EGF. The level of ERK-SPARK signal was correlated with the level of dually phosphorylated ERK measured by western blot, suggesting that ERK-SPARK can quantitatively measure ERK activity level.

To examine specificity of ERK-SPARK, cells were pre-incubated the with the ERK inhibitor PD 0325901, which abolished phase separation of the reporter upon addition of EGF. Pre-incubation with inhibitors for other MAPK family kinases, specifically the JNK inhibitor SB 203580 or the p38 inhibitor VIII, did not abolish formation of EGFP droplets upon addition of EGF. These results demonstrate that ERK-SPARK specifically reported ERK activity.

To investigate whether ERK-SPARK could detect GPCR-induced ERK activity, a hexapeptide full agonist for protease-activated receptor-1 was added to HEK293 cells. Time-lapse imaging revealed abundant EGFP droplets upon addition of the agonist; the signal peaked at around 6-9 minutes and dissolved between 15-20 minutes. These results demonstrated that ERK-SPARK detected transient ERK activity via endogenous PAR1 in HEK293 cells.

To determine whether the SPARK-based PKA and ERK reporters are applicable to in vivo imaging, PKA-SPARK and ERK-SPARK transgenic lines of Drosophila were created. The reporter fusion proteins were expressed in the air sac primordium (ASP) of the Drosophila tracheal system, where an essential mitogen and FGF-induced ERK signaling has been well established. To promote expression of the reporter in the ASP, the ERK-SPARK construct was expressed specifically in tracheal cells and EGFP droplets were detected in the ASP. Fluorescence imaging was conducted on an inverted microscope equipped with a confocal scanner unit, a digital CMOS camera, an automated stage, 20× dry (N.A. 0.75) objective, apochromatic confocal 40× WI λS water objective, apochromatic 60× oil objective, and laser inputs with laser lines at 488 nm for GFP imaging, 561 nm for mCherry imaging, and 642 nm for mIFP imaging. The confocal scanning unit was equipped with the following emission filters: 525/50-nm for GFP imaging, 610/60-nm for mCherry imaging, 732/68-nm for mIFP imaging. To confirm that the observed EGFP droplets resulted from a phosphorylation event, an ERK-unresponsive mutant of the reporter was expressed and no EGFP droplets were detected.

ERK-SPARK was also expressed in the Drosophila wing imaginal disc, a tissue that requires epidermal growth factor receptor (EGFR)-dependent signaling. Both normal ERK-SPARK and an inactive mutant form of ERK-SPARK were expressed. Whereas discs that expressed the mutant ERK-SPARK had no droplets, discs that expressed the normal ERK-SPARK had abundant fluorescent droplets. Most of the fluorescent droplets were at the dorsoventral boundary and distal hinge of the wing pouch, a pattern that overlaps with the regions that stain with antibody directed against dpERK.

To further demonstrate PKA-SPARK in live animals, the reporter was expressed in the wing imaginal discs and it was observed that cells in the pouch region of the wing discs had evenly distributed green fluorescence, suggesting expression of the reporter. Next, a constitutively active form of the alpha subunit of stimulatory G protein (Gαs*), which activates AC for cAMP production and results in PKA activation was expressed. EGFP droplets were detected in the wing discs subsequent to ectopic expression of Gαs*.

To demonstrate whether PKA-SPARK can be used in zebrafish, DNA encoding the reporter was injected into zebrafish embryos at the one-cell stage. Muscle cells at 24 hrs APF were imaged upon addition of isoprenaline, which showed EGFP droplet formation.

Typically, time-lapse imaging of live animals is technically challenging due to optical issues such as tissue autofluorescence and light scattering as well as rapid cell movements and shape changes, Since the SPARK reporters have large fluorescence change and a simple signal pattern that is readily detected, they can enable imaging of dynamic kinase activity in developing animals. To demonstrate ERK-SPARK for detection of dynamics of ERK signaling during animal development, the reporter system was expressed in the tracheal system of Drosophila because it undergoes metamorphosis at the pupal stage, and a previous study demonstrated that FGF signaling plays a critical role for tracheal development at metamorphosis. During this period, the tracheal imaginal progenitor cells in tracheal metameres 4 and 5 exit their niche and migrate posteriorly along the dorsal trunk. ERK-SPARK was expressed in the tracheal cells including the progenitors, and tracheal progenitors were marked with RFP. Fluorescence imaging of tracheal metamere 5 (Tr5) in live animals did not detected EGFP droplets in the pupal dorsal trunk cells immediately after puparium formation (APF). Time-lapse imaging showed that the EGFP droplets persisted for ~4 hrs, a time period when the tracheoblast progenitors migrated posteriorly. No EGFP droplets were detected between 4 and 7 hr APF, but at approximately 8 hr APF, EGFP droplets were again detected in the dorsal trunk; coinciding with the migration of tracheoblast progenitors of Tr4. These results demonstrate that the SPARK reporter can be used to image dynamic kinase signaling in a live animal during development.

Lastly the potential toxicity of the reporter was examined in animals. Data showed that viability of the transgenic fly was not affected when ERK-SPARK was expressed in the trachea, or in the whole animal.

In summary, the results demonstrate that the phase separation-based reporters achieve large fluorescence increase, high brightness and fast kinetics. Because of intensive fluorescence, simple signal pattern and rapid response, the reporters enable easy and robust visualization of dynamic kinase signaling in living animals in a qualitative way based on raw images with no requirement of quantitative data analysis.

In this example, the SPARK-PROTAC reporter system is demonstrated, which enables measurement of PROTAC formation of the ternary complex. This exemplary SPARK-PROTAC was made by genetically fusing the coiled coil-based homo-oligomeric HOTag3 (hexamer) to an E3 ligase and HOTag6 (tetramer), to a target protein. EGFP was included in both fusion proteins. Upon PROTAC-induced PPI between an E3 ligase and a target protein, each hexameric ligase-EGFP-HOTag3 recruits six target-EGFP-HOTag6. Then each tetrameric target-EGFP-HOTag6 recruits four ligase-EGFP-HOTag3, and so on. Eventually the HO-Tag-introduced multivalent aggregations driven by ligase/target interaction lead to EGFP phase separation, forming highly green fluorescent EGFP droplets.

To demonstrate SPARK-PROTAC, the ARV-825 PROTAC construct was used. ARV-825 comprises pomalidomide (an E3 ligase cereblon (CRBN)-binding IMiD) and OTX015 (a BRD4-binding ligand). ARV-825 thus induces interaction between CRBN and BRD4. HOTag3 was genetically fused to CRBN and HOTag6 was fused to the OTX015-binding BD1 domain of BRD4. Co-expression of the two HO-Tag fusion proteins revealed homogeneous fluorescence in the human embryonic kidney 293 (HEK293) cells, Addition of ARV-825 to the cells led to fast formation of EGFP droplets within a few minutes, indicated by the punctal green fluorescence. The intensive brightness (10×) and simple signal pattern allowed straightforward and robust detection of the PROTAC-induced interaction.

To show whether SPARK can quantitatively detect ARV-825 induced PPI, various concentrations of the PROTAC were added, ranging from 1 nM to 5 µM, and time-lapse fluorescence imaging was performed. At 1 nM, no EGFP droplets were detected. At 10 nM, small EGFP droplets were observed. At 30 nM, larger and more EGFP droplets formed. At 500 nM, large EGFP droplets were detected, and the EGFP fluorescence in the solution phase reduced significantly. This data show that SPARK may be used to quantitatively describe the PROTAC-induced PPI. To quantitatively analyze the data, we defined "SPARK signal" as the sum of fluorescent droplets' pixel intensity divided by sum of the cells' pixel intensity. Analysis of the imaging data using this formula revealed that the SPARK signal was dependent on ARV-825 concentration: the higher the concentration, the higher the SPARK signal. Plot of SPARK signal against ARV-825 concentration revealed a transition point around 0.03 to 0.1 nM.

EGFP Droplets Dissembled Over Time Upon Removal of the PROTAC.

Another PROTAC, dBET1, was designed by linking CRBN-binding IMiD and BRD4-binding ligand JQ1, which also induces interaction of CRBN and BRD4. ARV-825 was co-expressed the two fusion proteins (CRBN-EGFP-HOTag3, and BD1-EGFP-HOTag6 in HEK293 cells. Addition of dBET1 to the cells led to formation of EGFP droplets with intensive brightness and simple signal pattern, which allowed straightforward and robust detection of dBet1-induced interaction between CRBN and BRD4. Next, dBET1 was added at various concentrations of ranging from 200 nM to 20 µM, and higher concentration was required to induce EGFP droplets than for ARV-825. The results demonstrated that ARV-825 is more efficient in forming the PROTAC-induced ternary complex than dBET1, potentially due to differences in linker length of the two PROTACs between the two protein-binding moieties and/or difference in membrane permeability. Our data demonstrate that the reporter system of the invention can be used as a powerful live-cell assay for screening and comparing potent PROTACs.

The E3 ubiquitin ligase cereblon has previously been utilized in another class of molecules called immunomodulatory drugs or IMiDs (e.g. lenalidomide), which also induce protein-protein interactions and form ternary complexes, such as cereblon-lenalidomide-Ikaros. To show whether SPARK can detect IMiDs-induced protein-protein interactions, HOTag6 was genetically fused to the zinc finger domain 2 (ZF2) of ikaros (ZF2). Co-expression of CRBN-EGFP-HOTag3 and ZF2-EGFP-HOTag6 in HEK293 cells revealed homogenous fluorescence Addition of lenalidomide led to EGFP droplet formation within a few minutes, indicating that SPARK can also detect IMiDs-induced protein-protein interactions.

Many analogs and derivatives of IMiDs have recently been designed and explored as drug leads. CC-885, one IMiDs derivative, has been shown to induce interaction between CRBN and GSPT1-11. To examine whether SPARK can detect CC-885 induced protein-protein interactions, HOTag6 was genetically fused to GSPT1 and co-expressed with CRBN-EGFP-HOTag3 in HEK293 cells. Time-lapse imaging revealed that the co-expressed fusion proteins were homogeneously fluorescent. Addition of CC-885 led to intensely bright and punctal green fluorescence. Thus, SPARK also detects CC-885 induced protein-protein interactions. The result demonstrate that SPARK can be a powerful assay to screen IMiDs analogs and derivatives targeting specific proteins in live cells.

Lastly, after demonstrations of SPARK in detecting small molecule-induced protein-protein interactions, detection of small molecule-induced protein-protein dissociation by SPARK was tested. Tumorigenesis can be caused not only by stabilization of oncogenic proteins but also by destabilization of tumor suppressor proteins. It is therefore an objective to develop small molecules to stabilize tumor suppressors by induced dissociation with E3 ligases. One of the well-established examples for small molecule-based disruption of protein-protein interactions is Nutin-3a induced dissociation of HDM2 and p53. p53 interacts with the E3 ligase HDM2, resulting in ubiquitination and degradation. HDM2 is often overexpressed in many human cancers. Nutlin-3a thus stabilizes p53, and induces p53-dependent apoptosis.

An inducible SPARK system was developed by fusing: HOTag6 to the transactivation domain (TAD) of p53 and Frb (Frb-p53-HOTag6); HO-Tag3 to EGFP and FKBP12 (FKBP12-EGFP-HOTag3); and IFP2 (an improved infrared fluorescent protein) to the p53 binding domain (p53BD) of HDM2 (HDM2-IFP2). Co-expression of these three fusion constructs in the HEK293 cells led to homogeneous green and infrared fluorescence. Addition of rapamycin, which induces interaction between FKBP12 and Frb, resulted in rapid formation of green and infrared fluorescent droplets within a few minutes. Nutlin-3a was then added which led to rapid disassembly of the infrared fluorescent droplets with half-time~2 min, while the green fluorescent droplets were not affected by Nutlin-3a. This data demonstrated that SPARK detects Nutlin-3a induced dissociation of p53 and HDM2 and that SPARK may be used to screen for potent PPI inhibitors.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. A reporter system, wherein the reporter system is for detection of a protein-protein interaction between a first interacting protein and a second interacting protein, comprising
a first monomer comprising a fusion protein, wherein the fusion protein comprises:
a first coiled coil subunit that will spontaneously form a homo-oligomer with other coiled coil subunits of the same sequence; and
the first interacting protein;
and
a second monomer comprising a fusion protein, wherein the second fusion protein comprises:
a second coiled coil subunit that will spontaneously form a homo-oligomer with other coiled coil subunits of the same sequence; and
the second interacting protein;
wherein the first and second coiled coil subunits comprise different sequences;
wherein the first interacting protein and second interacting protein comprise the members of an interacting protein pair; and
wherein the first fusion protein, the second fusion protein, or both the first and second fusion proteins further comprises one or more reporter moieties.

2. The reporter system of claim 1, wherein the first coiled coil subunit and the second coiled coil subunits are selected from the group consisting of SEQ ID NO: 1-SEQ ID NO: 15.

3. The reporter system of claim 2, wherein the first and second coiled coil subunits are SEQ ID NO: 3 and SEQ ID NO: 6.

4. The pair of fusion proteins of claim 1, wherein the first interacting protein and the second interacting protein comprise a polypeptide selected from the group consisting of a whole protein, a protein fragment, and a protein domain.

5. The reporter system of claim 1, wherein the first interacting protein or the second interacting protein is activable.

6. The reporter system of claim 5, wherein wherein the first interacting protein or the second interacting protein is the substrate of an enzyme.

7. The reporter system of claim 6, wherein the enzyme is a kinase.

8. The reporter system of claim 1, wherein the first interacting protein is an E3 ubiquitin ligase and the second interacting protein comprises the target of a proteolysis targeting chimeras (PROTAC) construct.

9. The reporter system of claim 1, wherein in the first and/or second fusion proteins, any of the coiled coil subunit, the interacting protein, and the one or more reporter moieties are separated by a linker sequence.

10. The reporter system of claim 1, wherein the linker sequence comprises one or more repeats of SEQ ID NO: 16.

11. The reporter system of claim 1, wherein the first and second monomers are expressed as a single fusion protein comprising a self-cleaving moiety disposed between the first and the second fusion proteins.

12. The reporter system of claim 1, wherein the reporter system is expressed in a cell.

13. A method of detecting protein-protein interaction between a first interacting protein and a second interacting protein, comprising the steps of:
expressing a first monomer in the cell, wherein the first monomer is a fusion protein, wherein the fusion protein comprises: a first coiled coil subunit that will spontaneously form a homo-oligomer with other coiled coil subunits of the same sequence; and the first interacting protein;
expressing a second monomer in the cell, wherein the second monomer is a fusion protein, wherein the fusion protein comprises: a second coiled coil subunit that will spontaneously form a homo-oligomer with other coiled coil subunits of the same sequence; and the second interacting protein;

wherein the first and second coiled coil subunits comprise different sequences;

wherein the first monomer, the second monomer, or both the first and second monomers further comprises one or more reporter moieties; and by methods of detecting the one or more reporter moieties, observing the cell for the formation of localized punctae comprising phase-shifted droplets of concentrated aggregates of homo-oligomers of the first monomer and homo-oligomers of the second monomer, wherein the formation of the aggregations of punctae is driven by the interaction of the first interacting protein and the second interacting protein.

14. The method of claim 13, wherein
the first coiled coil subunit and the second coiled coil subunits are selected from the group consisting of SEQ ID NO: 1-SEQ ID NO: 15 and variants thereof.

15. The method of claim 14, wherein
the first and second coiled coil subunits are SEQ ID NO: 3 and SEQ ID NO: 6 or variants thereof.

16. The method of claim 13, wherein
the first interacting protein and the second interacting protein comprise a polypeptide selected from the group consisting of a whole protein, a protein fragment, and a protein domain.

17. The method of claim 13, wherein
the first interacting protein or the second interacting protein is an activable species.

18. The method of claim 17, wherein
the activable species is the substrate of an enzyme.

19. The method of claim 18, wherein
the enzyme is a kinase.

20. The method of claim 13, wherein
the observation is by time-lapse photography for a selected interval of time.

* * * * *

UNITED STATES PATENT AND TRADEMARK OFFICE
CERTIFICATE OF CORRECTION

PATENT NO. : 11,448,654 B2
APPLICATION NO. : 16/838023
DATED : September 20, 2022
INVENTOR(S) : Xiaokun Shu et al.

It is certified that error appears in the above-identified patent and that said Letters Patent is hereby corrected as shown below:

In the Claims

At Column 31, Line 63, "pair of fusion proteins" should be -- reporter system --.

At Column 32, Line 34, "wherein the" should be -- the --.

Signed and Sealed this
Second Day of May, 2023

*Katherine Kelly Vidal*
Katherine Kelly Vidal
*Director of the United States Patent and Trademark Office*